(12) United States Patent
Hageman et al.

(10) Patent No.: US 8,445,458 B2
(45) Date of Patent: May 21, 2013

(54) FOOD COMPOSITION FOR PRODROMAL DEMENTIA PATIENTS

(75) Inventors: Robert Johan Joseph Hageman, Wageningen (NL); Patrick Joseph Gerardus Hendrikus Kamphuis, Utrecht (NL); Ladislaus Maria Broersen, Utrecht (NL)

(73) Assignee: N. V. Nutricia, Zoetermeer (NL)

( * ) Notice: Subject to any disclaimer, the term of this patent is extended or adjusted under 35 U.S.C. 154(b) by 294 days.

(21) Appl. No.: 12/666,617

(22) PCT Filed: Jun. 20, 2008

(86) PCT No.: PCT/NL2008/050408
§ 371 (c)(1),
(2), (4) Date: Apr. 2, 2010

(87) PCT Pub. No.: WO2009/002164
PCT Pub. Date: Dec. 31, 2008

(65) Prior Publication Data
US 2010/0323982 A1    Dec. 23, 2010

(30) Foreign Application Priority Data
Jun. 27, 2007  (WO) ............... PCT/NL2007/050310

(51) Int. Cl.
*A01N 43/04* (2006.01)
*A61K 31/70* (2006.01)

(52) U.S. Cl.
USPC .............. 514/51; 514/42; 514/43; 514/49; 514/50

(58) Field of Classification Search
None
See application file for complete search history.

(56) References Cited

U.S. PATENT DOCUMENTS

| | | | |
|---|---|---|---|
| 3,600,197 | A | 8/1971 | Spangler, et al. |
| 5,886,037 | A | 3/1999 | Klor et al. |
| 6,689,467 | B1 | 2/2004 | Joubert et al. |
| 6,835,750 | B1 | 12/2004 | Henderson |
| 7,090,879 | B2 | 8/2006 | Albrecht et al. |
| 2003/0114415 | A1 | 6/2003 | Wurtman et al. |
| 2004/0001817 | A1 | 1/2004 | Giampapa |
| 2005/0208179 | A1 | 9/2005 | Albrecht et al. |
| 2006/0025376 | A1 | 2/2006 | Wurtman |
| 2006/0241077 | A1 | 10/2006 | Wurtman et al. |
| 2007/0004670 | A1 | 1/2007 | Wurtman et al. |
| 2007/0140992 | A1 | 6/2007 | Schick et al. |
| 2010/0331258 | A1 | 12/2010 | Kamphuis et al. |
| 2010/0331275 | A1 | 12/2010 | Groenendijk et al. |
| 2011/0009357 | A1 | 1/2011 | Hageman et al. |
| 2011/0027391 | A1 | 2/2011 | De Kort et al. |
| 2011/0105594 | A1 | 5/2011 | De Kort et al. |
| 2013/0012469 | A1 | 1/2013 | De Kort et al. |

FOREIGN PATENT DOCUMENTS

| | | |
|---|---|---|
| EP | 0 175 468 A2 | 3/1986 |
| EP | 1 216 041 B1 | 2/2004 |
| EP | 1656839 A1 | 5/2006 |
| EP | 1 666 092 A2 | 6/2006 |
| EP | 1800675 A1 | 6/2007 |
| EP | 1 282 365-81 | 12/2007 |
| JP | 64-080250 A | 3/1989 |
| JP | 06-237734 A | 8/1994 |
| JP | 10-004918 A | 1/1998 |
| JP | 10-136937 A | 5/1998 |
| JP | 11-071274 | 3/1999 |
| WO | WO-00/38829 A1 | 7/2000 |
| WO | WO-01/32034 A1 | 5/2001 |
| WO | WO 02/088159 A1 | 11/2002 |
| WO | WO-02/096464 A1 | 12/2002 |
| WO | WO-03/013276 A1 | 2/2003 |
| WO | WO-03/041701 A2 | 5/2003 |
| WO | WO-2005/039597 A2 | 5/2005 |
| WO | WO-2006/031683 A2 | 3/2006 |
| WO | WO-2006/118665 A2 | 11/2006 |
| WO | WO-2006/127620 A2 | 11/2006 |
| WO | WO-2007/001883 A2 | 1/2007 |
| WO | WO-2007/004685 A2 | 1/2007 |
| WO | WO-2007/004689 A1 | 1/2007 |
| WO | WO-2007/008586 A2 | 1/2007 |
| WO | WO-2007/058538 A2 | 5/2007 |
| WO | WO-2007/073178 A2 | 6/2007 |
| WO | WO-2009/002145 A2 | 12/2008 |
| WO | WO-2009/002146 A1 | 12/2008 |
| WO | WO-2009/002163 A1 | 12/2008 |
| WO | WO-2009/002165 A1 | 12/2008 |
| WO | WO-2009/002166 A1 | 12/2008 |
| WO | WO-2009/082203 A1 | 7/2009 |
| WO | WO-2009/082227 A1 | 7/2009 |

OTHER PUBLICATIONS

Quadri et al. Am. J. Clin. Nutr. (2004), vol. 80, pp. 112-122.*
U.S. Appl. No. 12/666,611, filed Dec. 23, 2009, Kamphuis, et al.
U.S. Appl. No. 12/666,619, filed Dec. 23, 2009, Hageman et al.
U.S. Appl. No. 12/666,621, filed Dec. 23, 2009, Groenendijk, et al.
International Search Report (PCT/NL2008/050406) dated Sep. 30, 2008.
International Search Report (PCT/NL2008/050410) dated Sep. 19, 2008.
International Search Report for PCT/NL2008/050411 dated Nov. 5, 2008.

(Continued)

*Primary Examiner* — Patrick Lewis
(74) *Attorney, Agent, or Firm* — Gilberto M. Villacorta; Sunit Talapatra; Foley & Lardner LLP

(57) ABSTRACT

A composition comprising (a) one or more ω-3 fatty acids selected from DHA, DPA and EPA, (b) uridine or its equivalent, and (c) a methyl donor, useful in the treatment of a person having characteristics of a prodromal dementia patient. The characteristics include e.g. a level of more than 350 ng Total-tau per liter cerebrospinal fluid (CSF), and a weight ratio of abeta-42/Phospho-tau-181 of less than 6.5 in CSF.

10 Claims, 1 Drawing Sheet

OTHER PUBLICATIONS

Katoku Y, et al. "Nutrient Compositions Containing Nucleic Acid Related Compounds, used for Growth and Health Maintenance—Contain e.g. Docosahexaenoic Acid, Arachidonic Acid and Cholesterol" WPI/Thomson, Jan. 13, 1998 (Abstract).
Wurtman, etal. "Synaptic Proteins and Phospholipids are Increased in Gerbil Brain by Administering Uridine Plus Docosahexaenoic Acid Orally" Brain Research (2006) pp. 83-92.
Database WPI Week 198918, Derwent Publications Ltd., London, GB, AN 1989-134762, JP 01 080250, Mar. 27, 1989 [XP002449815].
Database WPI Week 199439, Thomson Scientific, London, GB, AN 1994-312783, JP 06 237734, Aug. 30, 1994 [XP002494932], 2 pages.
Database WPI Week 199182, Derwent Publications Ltd., London, GB, AN 1998-123754, JP 10 004918, Jan. 13, 1998 [XP002470089], 1 page.
Database WPI Week 199831, Derwent Publications Ltd., London, GB, AN 1998-355002, JP 10 136937, May 26, 1998 [XP002449814].
Database WPI Week 199921, Thomson Scientific, London, GB, AN 1999-248435, JP 11 071274, Mar. 16, 1999 [XP002495741].
Folstein et al., "'Mini-Mental State' A Practical Method for Grading the Cognitive State of Patients for the Clinician," J Psychiat Res, 1975, 12(3), pp. 189-198.
Galasko et al., "An Inventory to Assess Activities of Daily Living for Clinical Trials in Alzheimer's Disease," Alz Dis Assoc Dis, 1997, 11(Sup 2), pp. 33-39.
Hansson et al., "Association Between CSF Biomarkers and Incipient Alzheimer's Disease in Patients with Mild Congnitive Impairment: A Follow-up Study," Lancet Neurol, vol. 5, No. 3, 2006, pp. 228-234.
International Search Report, PCT/NL2007/050310, dated Feb. 22, 2008, 3 pages.
McKahnn et al., "Clinical diagnosis of Alzheimer's disease: Report of the NINCDS-ADRDA Work Group," Neurology, 1984, 34, pp. 939-944.
Pratico et al., "Increase of Brain Oxidative Stress in Mild Cognitive Impairment," Arch Neurol, vol. 59, 2002, pp. 972-976.
"Derivative—Definition and More from the Free Merriam-Webster Dictionary" Retrieved Oct. 22, 2012 from http/www.merriam-webster.com/dictionary/derivative.
Cansev, M. et al. "Chronic Administration of Docosahexaenoic Acid or Eicosapentaenoic Acid, But Not Arachidonic Acid, Alone or in Combination with Uridine, Increases Brain Phosphatide and Synaptic Protein Levels in Gerbils", Neuroscience, 2007, vol. 148, pp. 421-431.
Korezyn, A. et al. "The prevention of the dementia epidemic", Journal of the Neurological Sciences, 2007, vol. 257, pp. 2-4.
Albert, M. et al. "Preclinical prediction of AD using neuropsychological tests", Journal of the International Neuropsychological Society, 2001, vol. 7, pp. 631-639.
Bird, T.D., Genetic aspects of Alzheimer disease, Genetics in Medicine, Apr. 2008, vol. 10, No. 4, p. 231-237.
Cansev, M. et al. "Oral administration of circulating precursors for membrane phosphatides can promote the synthesis of new brain synapses", Alzheimer's & Dementia, 2008, vol. 4, pp. S153-S168.
Cole, G. et al. "Docosahexaenoic Acid Protects From Amyloid and Dendritic Pathology In An Alzheimer's Disease Mouse Model", Nutrition and Health, 2006, vol. 18, pp. 249-259.
Freund-Levi, Y. et al. "w-3 Fatty Acid Treatment in 174 Patients With Mild to Moderate Alzheimer Disease: OmegAD Study", Arch Neurol, Oct. 2006, vol. 63, pp. 1402-1408.
Holguin, S. et al. "Chronic administration of DHA and UMP improves the impaired memory of environmentally impoverished rats", Behavioral Brain Research, 2008, vol. 191, pp. 11-16.
Markesbery, W. et al. "Neuropathologic Substrate of Mild Cognitive Impairment", Arch Neurol, Jan. 2006, vol. 63, pp. 38-46.
Morris, J. "Mild Cognitive Impairment Is Early-Stage Alzheimer Disease", Arch Neurol., 2006, vol. 63, No. 1, 6 pgs.
Nitsch, R. et al. "Evidence for a membrane defect in Alzheimer disease brain", Proc. Natl. Acad. Sci., Mar. 1992, vol. 89, pp. 1671-1675.
Oksman, M. "Impact of different saturated fatty acid, polyunsaturated fatty acid and cholesterol containing diets on beta-amyloid accumulation in APP/PS1 transgenic mice", Neurobiology of Disease, 2006, vol. 23, pp. 563-572.
Reynolds, E. "Vitamin B12, folic acid, and the nervous system", Review, Nov. 2006, vol. 5, pp. 949-960.
Sakamoto, T. et al. "Oral supplementation with docosahexaenoic acid and uridine-5'-monophosphate increases dendritic spine density in adult gerbil hippocampus", Brain Research, 2007, vol. 1182, pp. 50-59.
Wood-Kaczmar et al. Understanding the molecular causes of Parkinson's disease, Trends in Molecular Medicine, vol. 12, No. 11 (2006), pp. 521-528.
International Preliminary Report on Patentability corresponding to PCT/NL2008/050408, dated Sep. 15, 2009, 7 pages.
International Search Report corresponding to PCT/NL2008/050408, dated Aug. 8, 2008, 2 pages.

\* cited by examiner

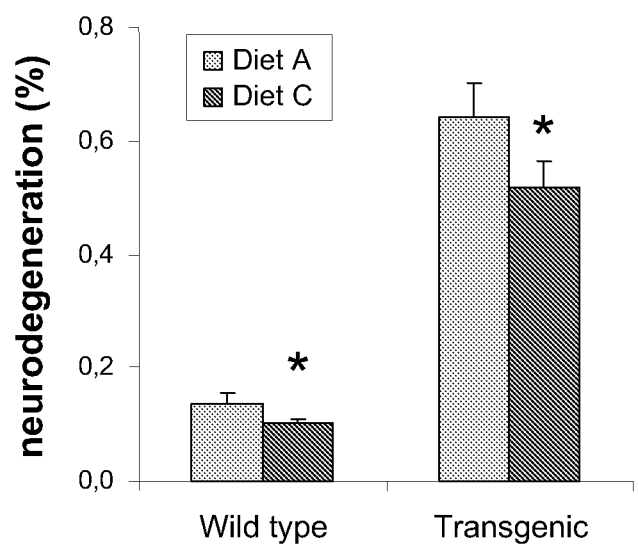

FOOD COMPOSITION FOR PRODROMAL DEMENTIA PATIENTS

CROSS-REFERENCE TO RELATED APPLICATIONS

This application is a National Stage application of PCT/NL2008/050408, file Jun. 20, 2008, which claims the benefit and priority of Patent Application PCT/NL2007/050310, filed Jun.27, 2007. The foregoing applications are incorporated by reference herein in their entirety.

FIELD OF THE INVENTION

The invention relates to the use of a fraction that comprises long chain polyunsaturated fatty acids and a fraction which comprises nucleotides or their equivalents and a methyl donor in the manufacture of a product which is used in the treatment of prodromal neurological patients, in particular prodromal dementia patients.

BACKGROUND

Many persons in the Western Society suffer from neurological diseases like non-AD-dementias, Alzheimer's disease (AD), Parkinson's disease (PD) or Huntington's disease (HD). These diseases are presently diagnosed by a clinician by careful interpretation of a range of symptoms, as defined in the Diagnostic and Statistical Manual of Mental Disorders (fourth Edition, 2000)—DSM-IV-TR) or in McKhann, et al., Report of the NINCDS-ARDA-workgroup, Neurology 1984, 34, 939-944.

Clear differences are observed between persons that suffer from specific types of memory impairment. For example, persons that suffer from Alzheimer's Disease suffer from neurodegeneration, which may be caused by accumulation of amyloid plaques or by neurofibrillary tangles or synaptic loss or atrophy in selected regions in the brain or enlargement of brain ventricles or mixtures of these phenomena. Patients who suffer from vascular dementia suffer from a decreased memory function which has been caused by an impaired cerebral blood flow and the ischemia and reperfusion events. Patients that suffer from dementia with Lewy Bodies or secondary dementias again have a pathology that differs from that of patients who experience the above-mentioned dementias, in terms of the cause, the nature of the damage to the brain and the overall symptoms, though they all demonstrate memory impairment.

In the diagnosis for a dementia, clinicians typically analyse, apart from memory function, at least also other cognitive domains, like ability to execute motor functions, to speak or to recognize objects, ability to function socially and to practice the activities that are considered to be normal in daily living.

Early in aging, in particular in elderly and typically above 60 years of age, mild symptoms of abnormalities in brain function or behaviour sometimes develop. The diffuse pattern of such symptoms may result in the diagnosis by a clinician, based on more or less accepted objective tests that such person suffers from a specific disease state. For example, persons who do not meet certain criteria in memory or cognition tests, but typically perform normal activities in daily life and suffer from no other pathologies, can be diagnosed as persons suffering from "mild cognitive impairment (MCI)". When the impairment occurs in a more systematic way and is thought to occur due to aging the diagnosis "Age-associated memory impairment" (AAMI) may be made. Some people consider MCI or AAMI as prodromal phase, i.e. a phase prior to but on the way towards the disease, of Alzheimer's disease. However, only less than 25% and in the majority of the cases less than 20% of this group of persons will eventually develop dementias. Part of the group of such "MCI persons" will recover and another part may remain a "MCI patient".

In this respect, it is submitted that in the context of this application, an elderly person is a person of the age of 50 or more, in particular of the age of 55 or more, more in particular of the age of 60 or more, more in particular of the age of 65 or more. This rather broad definition takes into account the fact that the average age varies between different populations, on different continents, etc. Most developed world countries have accepted the chronological age of 65 years as a definition of 'elderly' or older person (associated with the age at which one may begin to receive pension benefits), but like many westernized concepts, this does not adapt well to e.g. the situation in Africa. At the moment, there is no United Nations (UN) standard numerical criterion, but the UN agreed cut-off is 60+ years to refer to the older population in Western world. The more traditional African definitions of an elder or 'elderly' person correlate with the chronological ages of 50 to 65 years, depending on the setting, the region and the country.

The distinguishing tests for diagnosing prodromal patients do not coincide with conventional tests for diagnosing dementia or dementia-like disorders, though some of these conventional tests may further support the diagnosis of a prodromal patient for a neurological disorder or disease. For example, prodromal AD patients may score satisfactorily in a memory test, and will therefore not necessarily be MCI patients, whereas they may score positively in the present diagnostic tools for being prodromal. Then the diagnosis "prodromal dementia patient" is made. Such non-MCI group fulfilling the requirements of the diagnosis of a "prodromal dementia patient" has not been addressed by Hansson et al. published in http://neurology.thelancet.com, Feb. 6, 2006. The non-MCI group demonstrating the same score in the proposed tests was not investigated.

Diagnosing a patient as a so-called AAMI or MCI patient will relatively frequently result in false concerns that the patient automatically will become a dementia patient. False positive diagnosis also leads to relatively high costs to the society due to unnecessary measures that are taken to support these patients. Therefore a need exists to develop better diagnostic tools to identify the various types of brain diseases or disorders which may occur in a person during aging and to identify the prognosis, which belongs to a specific preclinical phase. Also a need exists to support the unique group of prodromal dementia patients, to decrease the likelihood that they will develop a form of senile dementia.

WO 2007/008586 discloses a method to reduce the level of amyloid beta peptide in an individual comprising administering a source of docosahexaenoic acid and docosa-pentaenoic acid ω-6. WO 2006/031683 discloses the use of a uridine, preferably in combination with choline for improving a cognitive or neurological function. WO 2006/127620 discloses a composition comprising DHA and UMP for the treatment of a subject with a memory disorder, learning problems, or a neurological disorder, such as an Alzheimer patient. Wurtman et al., *Brain Research* 2006, 1088(1), 83-92 disclose a combination of choline, UMP and DHA being able to enhance the quantity of synaptic proteins and phospholipids in gerbil brains and being potentially useful in treating Alzheimer's disease. WO 03/041701 discloses a composition comprising DHA, EPA, choline, methionine, vitamin B6, folic acid, zinc, magnesium and UMP as alternative for nucleobases for the treatment of Parkinson's disease, epilepsy, schizophrenia, paranoia, depression, sleep disorders, psychoses, dementia, ADHA, impaired memory function, chronic fatigue syndrome and motoric disorders.

However, nowhere in the art a suggestion has been made to use these fractions for the treatment of prodromal dementia patients, which have specific lesions in the neuro-logical system, for example in the brain or experience specific biochemical pathologies.

SUMMARY OF THE INVENTION

The invention is based on an early distinction of disorders which, in the absence of effective treatment, have a high probability to develop into neurological disorders such as dementia, in particular Alzheimer's disease (AD), among disorders such as mild cognitive impairment (MCI) which do not necessarily ultimately lead to dementia. It has now been found that such prodromal patients of neurological disorders benefit from the administration of a product containing long-chain polyunsaturated fatty acids, nucleotides and methyl donors. Such administration decreases the development of more severe problems that are associated with brain malfunction, such as memory and cognition problems, tremor, decrease of intensity in feelings and sensations, and may decrease or delay the incidence of dementias.

BREIF DESCRIPTION OF THE DRAWINGS

FIG. 1 shows the percentage of neurodegeneration in the neocortex of APP/PS1 transgenic mice and their wild type littermates fed Diet A (regular rodent chow) or Diet C (supplemented regular rodent chow).

DESCRIPTION OF THE INVENTION

The invention pertains to a composition comprising (a) one or more ω-3 fatty acids, (b) uridine or cytidine or their equivalents, and (c) a methyl donor, for use in the prevention or delay of the onset of dementia in a person having characteristics of a prodromal dementia patient.

For the purpose of the invention, persons that suffer from "senile dementia" are defined as suffering from one or more dementias. Senile dementia or dementia is considered to comprise Alzheimer's disease (AD). Therefore, the invention also pertains to a composition comprising (a) one or more ω-3 fatty acids, (b) uridine or cytidine or their equivalents, and (c) a methyl donor, for use in the prevention or delay of the onset of Alzheimer in a person having characteristics of a prodromal Alzheimer patient.

Nevertheless, the invention is independently directed at prodromal dementia patients and/or prodromal Alzheimer patients. A "prodromal dementia patient" is a person who does not suffer from a senile dementia as defined above, but has an increased likelihood to develop senile dementia. Likewise a "prodromal Alzheimer patient" is a person who does not suffer from AD, but has an increased likelihood to develop AD. The diagnostic tools that are used to classify the patients as prodromal patients are described below and include an accurate diagnosis of brain lesions and biochemical problems and careful setting of criteria.

Prodromal patients according to the invention are defined to be persons that score positively on at least one, preferably at least two, more preferably at least three of the following criteria:

a level of more than 350 ng Total-tau per liter cerebrospinal fluid (CSF);

a weight ratio of abeta-42/Phospho-tau-181 of less than 6.5 in CSF;

presence of medial temporal lobe (MTL) atrophy, existing of volume loss of hippocampus, entorhinal cortex, or amygdala evidenced on Magnetic Resonance Imaging (MRI) with either qualitative ratings using visual scoring (referenced to well characterised population with age norms) or quantitative volumetry of regions of interest (referenced to well characterized population with age norms)

presence of fronto-temporal lobe (FTL) atrophy evidenced on MRI with qualitative ratings or quantitative volumetry;

a level of more than 25 pg F2-iso-prostane (F2-IsoP, iso-prostane 8,12-iso-iPF2alpha-VI) per mL CSF.

Further explanations of the significance of concentrations of T-tau, P-tau 181, Abeta42 and F2-Isoprostane in CSF for future development of Alzheimer's disease can be found in: Hansson 0, Zetterberg H, Buchhave P, Londos E, Blennow K, Minthon L (2006) Association between CSF biomarkers and incipient Alzheimer's disease in patients with mild cognitive impairment: a follow-up study. Lancet Neurol 5:228-234; and in Pratico D, Clark C M, Liun F, Lee V Y M, Trojanowski J Q (2002) Increase in brain oxidative stress in mild cognitive impairment: a possible predictor of Alzheimer disease. Arch Neurol 59:972-976.

In a preferred embodiment, the identification of prodromal patients according to the invention comprises at least the first two criteria (total tau and ratio abeta-42/P-tau-181). More preferably, one of the three other criteria (MTL atrophy, FTL atrophy, F2-IsoP) is also applied.

In addition to or instead of one or more of the above criteria, the following can be advantageously used:

reduced glucose metabolism in bilateral temporal parietal areas of the brain, as is detectable by Positron Emission Tomography (PET);

reduced glucose metabolism in the posterior cingulate cortex, as is detectable by PET;

impaired blood flow in the brain as measurable by applying Single-Photon Emission Computed Tomography (SPECT), for example by applying the radioisotope 99mTc-HMPAO);

impaired glucose metabolism in the brain as measurable by applying SPECT;

abnormalities in the histology of the medial or inferior temporal lobes as can be determined by MRI or in the rate of glucose utilisation;

abnormalities in histology or glucose utilization in the temporal parietal cortex or posterior cingulate cortex.

Abnormalities in the condition of the brain or parts thereof can be established by either taking the person's own condition under healthy circumstances as a reference, or, when this is not available, by taking the average condition of a representative group (so matched for e.g. age) as a reference. The latter will occur most frequently. By comparison of the patient's condition with the reference situation and the average situation when the pathological condition would have been developed to its full extent, the clinician is capable of recognizing a prodromal phase. In particular an intermediate situation wherein the patient demonstrates a deviation of x % from the value of a healthy individual in the direction of the pathological conditions is for the purpose of this invention considered to be a prodromal patient. The value of x for the determination of blood flow and glucose metabolism is 20% when determined under standardised conditions in terms of feeding and exercise.

It should be noted that the score of these prodromal patients in tests relating to the presence of episodic memory impairment or other tests suitable for the judgment of the presence of the neurological disease, does not meet the criteria for diagnosing a severe neurological disease like Alzheimer's Disease, Parkinson's Disease or Huntington's Disease.

LC-PUFA

The LCP to be used preferably comprise at least one LCP selected from docosa-hexaenoic acid (22:6 ω-3; DHA), docosapentaenoic acid (22:5 ω-3; DPA) and eicosapentaenoic acid (20:5 ω-3; EPA). Preferably the present composition contains at least DHA, preferably DHA and EPA. More preferably the composition contains DHA and at least one precursor of DHA selected from EPA and DPA, more preferably the present composition comprises DHA, DPA and EPA. The inventors recognized that only part of the DHA incorporated in the brain is from orally ingested DHA. An important part of the DHA incorporated in the brain is derived from conversion of DPA to DHA in the brain. In a further aspect the present composition preferably contains a significant amount of EPA. EPA is converted to DPA (ω-3), increasing subsequent conversion of DPA (ω-3) to DHA in the brain. Hence, the present composition preferably also contains a significant amount of EPA, so to further stimulate in-vivo DHA formation.

The LCP is preferably provided as triglycerides, diglycerides, monoglycerides, free fatty acids or their salts or esters, phospholipids, lysophospholipids, glycerol ethers, lipoproteins, ceramides, glycolipids or combinations thereof. Preferably, the present composition comprises at least DHA in triglyceride form.

The present method preferably comprises the administration of 400-5000 mg (DHA+EPA) per day, more preferably 500-3000 mg per day, most preferably 1000-2500 mg per day. The proportion of (DHA+EPA) of the total fatty acids is preferably 5-50 wt. %, more preferably 10-45 wt. %, most preferably 15-40 wt. %. The present method preferably comprises the administration of DHA, preferably in an amount of 300-4000 mg per day, more preferably 500-2500 mg per day.

An amount per day as described herein means an amount in a daily dosage unit provided by the composition of the invention. Such a daily dosage unit may be a single dosage, but it may also be divided over two or three, or even more daily servings. If the composition, as according to a preferred embodiment, is intended for administration as a single unit, the amounts per day as described herein, are preferably the amounts present in the (preferably packaged) composition unit.

The present composition preferably comprises 1-40 wt. % DHA based on total fatty acids, preferably 3-36 wt. % DHA based on total fatty acids, more preferably 10-30 wt. % DHA based on total fatty acids. The present composition preferably comprises 0.5-20 wt. % EPA based on total fatty acids, preferably 2-10 wt. % EPA based on total fatty acids, more preferably 5-10 wt. % EPA based on total fatty acids. The ratio of the weights of DHA to the sum of EPA and DPA (ω-3) is preferably larger than 1.0, more preferably 1.2-10, more preferably 2-8. The above-mentioned ratios and amounts take into account and optimise several aspects, including taste (too high LCP levels reduce taste, resulting in a reduced compliance), balance between DHA and precursors thereof to ensure optimal effectiveness in relation to maximum dosage and possibility of product formulations such as liquid form, bar or capsule.

The present composition preferably contains a very low amount of arachidonic acid (AA; 20:4 ω-6). Arachidonic acid is believed to counteract the effects of the present composition. The present subjects normally ingest sufficient (precursors of) AA, and an excess daily dosage may stimulate inflammatory responses, inhibiting daily activities. Preferably the weight ratio DHA/AA in the present composition is at least 5, preferably at least 10, more preferably at least 15, up to e.g. 100. Preferably, the weight ratio EPA/AA is at least 2. The present method preferably comprises the administration of a composition comprising less than 5 wt. % arachidonic acid based on total fatty acids, more preferably below 2.5 wt. %. The ratio ω-6/ω-3 fatty acids in the present product is advantageously below 0.5, preferably below 0.2, e.g. down to 0.05 or to 0.1. The amounts of ω-3 and ω-6 fatty acids herein apply to the sum of all ω-3 or ω-6 fatty acids, respectively, having at least two double bonds and at least 20 carbon atoms. The ratio ω-6/ω-3 fatty acids (C 20 and higher) in the present product is preferably below 0.3, more preferably below 0.15, e.g. down to 0.03 or to 0.06. If the C18 fatty acids are included, the preferred ω-6/ω-3 weight ratio is 0.05-1, more preferably 0.1-0.6, most preferably 0.15-0.4.

The present composition preferably contains at least one oil selected from fish oil, algae oil and eggs lipids. Preferably the present composition contains fish oil comprising DHA, EPA and preferably DPA.

Saturated and Monounsaturated Fatty Acids

The present composition preferably comprises saturated and/or mono-unsaturated fatty acids. The amount of saturated fatty acids is preferably 6-60 wt. % based on total fatty acids, preferably 12-40 wt. %, more preferably 20-40 wt. % based on total fatty acids. In particular the amount of C14:0 (myristic acid)+C16:0 (palmitic acid) is preferably 5-50 wt. %, preferably 8-36, more preferably 15-30 wt. % wt. % based on total fatty acids. The total amount of monounsaturated fatty acids, such as oleic acid and palmitoleic acid, is preferably between 5 and 40 wt. %, more preferably between 15 and 30 wt. %. Including of the saturated and/or monounsaturated fatty acids provides an energy source, assisting the activities of prodromal subjects.

Phospholipids

Preferably, the present composition preferably comprises phospholipids, preferably 0.1-50 wt. % phospholipids based o, n total weight of lipids, more preferably 0.5-20 wt. %, more preferably between 1 and 5 wt. % based on total weight of lipids. The total amount of lipids is preferably between 10 and 30 wt. % on dry matter, and/or between 2 and 6 g lipid per 100 ml for a liquid composition. Inclusion of phospholipids beneficially improves membrane function, thereby enabling an improved functioning of the different parts of the brain that may be affected in prodromal subjects. Furthermore, the phospholipids improve stability of the present product. Phospholipids further enable the manufacturing of palatable products. Also, phospholipids are a source for choline and prevent the decline in plasma choline levels after exercise. Choline is necessary for the formation of acetylcholine, a neurotransmitter involved in learning and memory and in the activation of muscles. These advantages are already achieved at relatively low phospholipid levels.

Nucleotides

Preferably the present composition comprises nucleosides and equivalents thereof. Equivalents include nucleotides, nucleobases, nucleosides and phosphorylated and/or acylated forms. All such equivalents are capable of increasing endogenous levels of the active forms of nucleosides in body, tissues such as blood, liver and brain. Useful ingredients include extracts of plant, animal, bacterial, algal or yeast material, as well as synthetic compounds.

The present composition preferably comprises uridine and/or an equivalent thereof, preferably at least one uridine or an equivalent thereof selected from the group consisting of uridine (i.e. ribosyl uracil), deoxyuridine (deoxyribosyl uracil), uridine phosphates (UMP, dUMP, UDP, UTP), nucleobase uracil and acylated uridine derivatives. Preferably the present composition comprises an uridine phosphate selected from uridine monophosphate (UMP), uridine diphosphate (UDP and uridine triphosphate (UTP). Most preferably the present composition comprises UMP, as UMP is most efficiently being taken up by the body. Hence, inclusion of UMP in the present product enables a high effectively at the lowest dosage and/or the administration of a low volume to the subject. Preferably at least 50 wt. % of the uridine in the present composition is provided by UMP, more preferably at least 75 wt. %, most preferably at least 95 wt. %. The present method preferably comprises the administration of uridine (the cumulative amount of uridine, deoxyuridine, uridine phosphates, uracil and acylated uridine derivatives) in an amount of 0.08-3 g per day, preferably 0.1-2 g per day, more preferably 0.2-1 g per day.

The present method preferably comprises the administration of a composition comprising uridine in an amount of 0.08-3 g UMP per 100 ml liquid product, preferably 0.1-2 g UMP per 100 ml liquid product, more preferably 0.2-1 g per 100 ml liquid product. Preferably 1-37.5 mg UMP per kilogram body weight is administered per day. The required dosages of the equivalents on a weight base can be calculated from the dose for UMP by taking equimolar amounts using the molecular weight of the equivalent and of UMP, the latter being 324 Dalton. The amount of nucleotides or nucleosides and derivatives is preferably 3-115 μmol, preferably 5-35 μmol per kg body weight per day, or 0.25 to 9 mmol, preferably 0.3-6, most preferably 0.45-2.8 mmol per day. Uridine derivatives like UDP, which is readily formed from dietetic UMP, appear to be important for transport of glycoproteins and glycolipids within the cell and availability thereof in the cytosol and plasma membrane.

Preferably the weight ratio of uridine to cytidine is larger that 1.0, more preferably at least 2.0, most preferably more than 5.0. The term uridine as used herein relates to uridine and/or equivalents thereof as explained above. The term cytidine as used herein relates to cytidine and/or equivalent thereof. Although cytidine is a precursor of uridine, which passes the blood brain barrier, it is more efficient and effective to include uridine in the present composition.

In a further preferred embodiment the present composition preferably does not contain high amounts of other nucleotides. Hence, preferably the weight ratio adenosine/uridine in the present composition is below 0.1, more preferably below 0.01, most preferably 0. Preferably the weight ratio guanosine/uridine in the present composition is below 0.1, more preferably below 0.01, most preferably 0. Preferably the weight ratio of inosine to uridine in the present composition is below 0.1, more preferably below 0.01, most preferably 0.

Combination of Uridine and LCP

It was found by the inventors that the nucleotide equivalents as defined, and in particular the uridine sources as defined are important to support and/or enhance the effect of the lipid fractions as defined above on daily activities. The present combination, particularly of (i) uridine and (ii) DHA and/or EPA is surprisingly effective. On a biochemical level this may be observed by an improvement of ceramide metabolism in membranes and in particular an increase in glycolipids at the expense of the presence of simple ceramides.

Methyl Donors

Preferably the present composition contains methyl donors. Methyl donors are those food grade compounds which are capable of providing a methyl, methylene or formyl group when administered to a human individual in vivo. The methyl donor included in the present composition is preferably selected from serine, methionine, choline, betaine, dimethylglycine and sarcosine and derivatives thereof. The methyl donors can be included in the formula as pure compounds as such, as their salts and as compounds, wherein the methyl donor is covalently bound to amino acids, and which have a molecular weight less than 600 Dalton.

Preferably the present composition contains choline and/or phosphatidylcholine. The present method preferably comprises the administration of more than 50 mg choline per day, preferably 80-2000 mg choline per day, more preferably 120-1000 mg choline per day, most preferably 150-600 mg choline per day. The present composition preferably comprises 50 mg to 3 gram choline per 100 ml of the liquid formula, preferably 200 mg -1000 mg choline/100 ml. The dose of the other methyl donors can be calculated by taking equimolar amounts as defined for choline and correcting for the molecular weight of that methyl donor.

Supplying choline with the diet increases the plasma choline and thereby prevents membrane breakdown. The use of the selected methyl donors will increase the number of patients that respond to the therapy. Especially elderly, in particular frail elderly, benefit from the inclusion of the selected methyl donors.

Minerals & Trace Elements

The present composition can be further improved by including one or more minerals. Preferably the present composition comprises at least one mineral selected from zinc, magnesium, copper, manganese and molybdenum. Preferably the present composition comprises manganese and molybdenum.

Manganese

Inclusion of manganese in a diet is important for improving membrane function of cells, in particular the membrane function of nerve cells. Especially those persons that are malnourished or have an inherited or metabolic disorder involving imparted metabolic capacity for producing sphingomyelin and/or related compounds like sulfatides and glycosylated ceramides, benefit from inclusion of the mineral fraction. The amount of manganese administered per day is preferably more than 0.1 mg, more preferably 0.1-1 mg. Preferably the present method comprises the administration of a (liquid) composition comprising 0.05 to 2 mg manganese per 100 ml, preferably 0.1-1 mg manganese per 100 ml.

Molybdenum

Additional molybdenum is strongly preferred to allow proper functioning of the cofactors, which appears important for creating a proper composition of the membranes, e.g. their sulfatide content, and in particular ensures a proper functioning of nerve cells. Further, inclusion of a proper amount of molybdenum delays brain shrinkage in part of the elderly during aging. The present method preferably comprises the administration of a composition comprising 0.1-100 microgram molybdenum per 100 ml, preferably 1-50 microgram molybdenum per 100 ml.

Zinc

It is also preferred to include additional zinc into the product which comprises the lipids or nucleotide fraction as described above, in order to stabilize proteins in the brain and prevent agglomeration thereof, which could impart daily life activities. The present method preferably comprises the administration of a composition comprising 0.05 mg-25 mg zinc per 100 ml, preferably 0.1-10 mg zinc per 100 ml.

Vitamins

The composition may advantageously contain vitamins, such as vitamin C, vitamin E and B vitamins. Advantageously, vitamin B12 and folate are included because low plasma B12/folate levels are a risk factor for the development of AD.

The present composition preferably comprises 50-1000 μg folic acid, more preferably 150-750 μg, most preferably 200-500 μg folic acid, per 100 g liquid product. The present method preferably comprises the administration 50-1000 μg folic acid per day, more preferably 150-750 μg, most preferably 200-500 μg folic acid per day. The present composition preferably comprises 0.5-15 μg vitamin B12, more preferably 1-10 μg, most preferably 1.5-5 μg vitamin B12, per 100 g liquid product. The present method preferably comprises the administration 0.5-15 μg vitamin B12 per day, more preferably 1-10 μg, most preferably 1.5-5 μg vitamin B12 per day.

Product

The present composition is preferably a ready-to-use liquid, solid, or semi-liquid product. It can also be in a concentrated form suitable for dissolving or dilution or suitable for the purpose of fortifying a second product. The preparation can be a drink, an emulsion, a dispersion, a pill or capsule, a bar, a powder, granulated or not, a pudding, a sauce, a gel, an ice cream, a soup, a cookie, a lollipop, sweetie, or other form known in the art. The present composition is preferably enterally administered, more preferably orally. Most preferably the present composition is administered through a straw. The product is preferably used as a supplement, having a dry weight of a daily dosage unit preferably between 10 and 50, more preferably between 15 and 35 g. When it is a ready-to-use liquid, the daily liquid amount is preferably between 75 and 200 ml per day or per unit, most preferably between 90 and 150 ml/day.

The subjects that can benefit from the method and composition of the invention (e.g. prodromal Alzheimer's disease patients, prodromal dementia patients, and elderly persons, in particular persons above 65 years of age) often experience problems with eating. Their sensory capabilities and/or control of muscles can become imparted, as well as in some instances their ambition to apply proper eating habits. Swallowing and/or mastication may be problematic. Hence, the present composition is preferably provided in the form of a drink capable of being ingested through a straw.

The composition for use according to the invention preferably has a low viscosity, preferably a viscosity between 1 and 2000 mPa.s measured at a shear rate of 100 sec$^{-1}$ at 20° C. More preferably, the present composition is preferably provided in the form of a drink capable of being ingested through a straw which makes the product even easier to ingest and improves compliance. In a preferred embodiment the present composition has a viscosity of 1-80 mPas at a shear rate of 100 per sec at 20° C., more preferably of 1-40 mPas at a shear rate of 100 per sec at 20° C. To be optimally accepted by the patient, the present composition preferably has an osmolality of 300 to 800 mOsm/kg.

Additionally many of the subjects (prodromal Alzheimer's disease patients, prodromal dementia patients and elderly persons, in particular persons above 65 years of age) experience a general loss in appetite and/or become malnourished. Hence it is advantageous to include within the present composition other nutrients. However, the energy density of the product is preferably not so high that it interferes with normal eating habits. When in liquid form, the present product preferably contains between 0.2 and 3 kcal/ml, more preferably between 0.5 and 2, between 0.7 and 1.5 kcal/ml.

Advantageously the present composition contains digestible carbohydrates. The digestible carbohydrates positively influence the operational skills of the subject, and have an advantageous effect over and above the effects for the present composition containing LCP and/or uridine. The present composition preferably contains between 1 and 50 gram digestible carbohydrates per 100 ml of a liquid product, more preferably between 5 and 30 grams per 100 ml, more preferably 10-30 grams carbohydrates/100 ml. The total amount of digestible carbohydrates is preferably between 25 and 80 wt. % on dry matter, preferably 40-80 wt. % based on dry matter.

The present composition may further comprise protein, preferably 0.5-10 g protein per 100 ml, more preferably 1-6 gram protein per 100 ml, most preferably 2-6 gram protein/ 100 ml. Preferably the present composition contain at least 80 wt. % milk derived protein (e.g. whey and/or casein) based on total protein. Proteins enable the manufacturing of palatable products, especially for frail elderly.

Suitably the present product has a cumulative amount of uridine and lipids and methyl donors (choline) of at least 20, preferably 40-90, more preferably 45-80 wt % of the total dry mass of the product. Such products are especially useful as such product does not disturb the critical eating patterns of the subject. Additionally these products may also allow for convenient fortification of second dishes or second meals. Suitable forms of such products are powders and a gel.

Persons suffering from neuropathies or neurological problems often experience problems with eating. Their sensory capabilities and/or control of muscles has become imparted, as well as in some instances their ambition to apply proper eating habits. Part of these patients may experience a general loss in appetite and a relatively large part of this patient group became malnourished. Preferably the product for malnourished persons has an energy density of 1.6-4.5 kcal per g product.

EXAMPLES

Example 1

Capsule for a Patient Diagnosed as a Prodromal Dementia Patient

Coating of a slowly dissolvable polymeric material surrounding a liquid phase, wherein the liquid is 1.1 g and comprises:
0.8 g of a lipid blend of vegetable oil and marine oil giving as fatty acid profile:
Saturated fatty acids 34 g
Oleic acid 15 g
Eicosapentaenoic acid 7 g
Docosahexaenoic acid 27 g
Linoleic acid 2.6 g
Alpha-linolenic acid 0.6 g
Other fatty acids make up to 100 g fatty acids
200 mg uridine monophosphate
50 mg choline
50 mg other components (including folic acid, vitamin B12, vitamin B6, minerals, trace elements).

Example 2

Gel for Forting a Second Dish

The gel contains a lipid fraction, a nucleotide fraction, a methyl donor and a mineral fraction in an amount of per 10 g:

100 mg DHA 100 mg UMP 50 mg choline

40 µg folic acid 50 mg magnesium aspartate.

The gel can be added to a soup or meat sauce to fortify a warm dish. The support of the daily activities in the life of an elderly susceptible of developing dementia can be determined by measuring the ease of applying these activities after administration of the product for a period of preferably at least 2 weeks.

Example 3

Supplement with Package

Packaged composition comprising per 125 ml:

Energy 125 kcal; Protein 3.9 g; Carbohydrate 16.5 g; Fat 4.9 g.

Fat includes 1.5 g DHA+EPA, and 106 mg phospholipids (soy lecithin); Choline 400 mg; UMP (uridine monophosphate) 625 mg; Vitamin E 40 mg α-TE; Vitamin C 80 mg; Selenium 60 µg; Vitamin B12 3 µg; Vitamin B6 1 mg; Folic acid 400 µg.

Minerals and trace elements: Sodium 125 mg; Potassium 187.5 mg; Chloride 156.3 mg; Calcium 100 mg; Phosphorus 87.5 mg; Magnesium 25 mg; Iron 2 mg; Zinc 1.5 mg; Copper 225 µg; Manganese 0.41 mg; Molybdenum 12.5 µg; Chromium 8.4 µg; Iodine 16.3 µg. Vitamins: Vit. A 200 µg-RE; vit. D3 0.9 µg; vit. K 6.6 µg; Thiamin (B1) 0.19 mg; Riboflavin (B2) 0.2 mg; Niacin (B3) 2.25 mg-NE; Pantothenic acid (B5) 0.66 mg; Biotin 5 µg.

The package indicates that the composition improves the activities of daily living. The composition is suitable for administration to prodromal dementia patients, prodromal Alzheimer patients and elderly as determined using the tests described above. Recommended dosage is one, two or three packages per day.

Experiment 4

Diet-Induced Changes in Neurodegeneration in a Model of Prodromal Alzheimer's Disease Young female APP/PS1 transgenic mice and their wild type littermate controls were either fed Diet A (control chow) or Diet C with additives as indicated in Table 1. Three months after the start of the dietary intervention, mice were sacrificed and brains were collected. At this stage mice were only six months of age, at which they show no signs of either behavioural disturbances or cognitive deficits. Only at an age of ten months, the first memory deficits become apparent in these mice [Oksman et al. Neurobiology of Disease 23 (2006) 563-572]. The Amino Cupric Silver staining was used to visualize neurodegenerative processes in sections of the brain. Image analysis and stereology were used for quantification of neurodegeneration in the neocortex.

TABLE 1

Overview of the amounts of specific nutrients that were added to a regular rodent chow to create Diet C. Diet A represents the regular rodent chow. The diets were made isocaloric.

| Additives (g/100 g diet) | Diet A | Diet C |
| --- | --- | --- |
| DHA | — | 0.757 |
| EPA | — | 0.189 |
| UMP | — | 1.000 |
| choline | — | 0.313 |
| lecithin | — | 0.412 |
| vitamin E | — | 0.157 |
| vitamin C | — | 0.160 |
| selenium | — | 0.0001110 |
| folate | — | 0.0007000 |
| vitamin B6 | — | 0.0027000 |
| vitamin B12 | — | 0.0000011 |

Diet C induced a significant decrease in neurodegeneration in the neocortex of both young APP/PS1 transgenic mice and their wild type littermates. Data is presented in FIG. 1. The present data indicate that this dietary intervention can be used to reduce neurodegenerative processes that precede the development of Alzheimer's disease. Moreover, neurodegeneration was reduced in young APP/PS1 transgenic mice before the onset of behavioural or cognitive changes, as well as in wild type control mice, underlining the relevance of this dietary intervention for the prodromal stages of Alzheimer's disease.

The invention claimed is:

1. A method for the prevention or delay of the onset of dementia in a person having characteristics of a prodromal dementia patient comprising administering to the person a composition comprising:
    (a) one or more ω-3 fatty acids selected from DHA, DPA and EPA,
    (b) a uridine selected from the group of uridine, deoxyuridine, uridine phosphates, uracil and acylated uridine derivatives, and
    (c) a methyl donor.

2. The method according to claim 1, wherein the characteristics comprise two or more of:
    a level of more than 350 ng Total-tau per liter cerebrospinal fluid (CSF);
    a weight ratio of abeta-42/Phospho-tau-181 of less than 6.5 in CSF;
    presence of medial temporal lobe (MTL) atrophy, existing of volume loss of hippocampus, entorhinal cortex, or amygdala evidenced on Magnetic Resonance Imaging (MRI);
    presence of fronto-temporal lobe (FTL) atrophy evidenced on MRI with qualitative ratings or quantitative volumetry;
    a level of more than 25 pg F2-iso-prostane (F2-IsoP, isoprostane 8,12-iso-iPF2alpha-VI) per mL CSF;
    reduced glucose metabolism in bilateral temporal parietal areas of the brain, as is detectable by Positron Emission Tomography (PET);
    reduced glucose metabolism in the posterior cingulate cortex, as is detectable by PET;
    impaired blood flow in the brain as measurable by applying Single-Photon Emission Computed Tomography (SPECT), for example by applying the radioisotope 99mTc-HMPAO);
    impaired glucose metabolism in the brain as measurable by applying SPECT;

abnormalities in the histology of the medial or inferior temporal lobes as can be determined by MRI or in the rate of glucose utilisation;

abnormalities in histology or glucose utilization in the temporal parietal cortex or posterior cingulate cortex.

3. The method according to claim 1, wherein the composition comprises 0.1-2 g uridine, calculated as uridine monophosphate, per daily dosage unit.

4. The method according to claim 1, wherein the composition comprises 400-4000 mg of the sum of DHA, DPA and EPA per daily dosage unit.

5. The method according to claim 1, wherein the composition comprises 300-3600 mg DHA per daily dosage unit.

6. The method according to claim 1, wherein the composition further comprises arachidonic acid (AA).

7. The method according to claim 6, having a DHA to arachidonic acid weight ratio of at least 5.0.

8. The method according to claim 1, wherein the methyl donor is choline.

9. The method according to claim 1, wherein the composition further comprises one or more B vitamins.

10. The method according to claim 8, wherein the choline is present in a daily amount of 80-2000 mg.

\* \* \* \* \*

UNITED STATES PATENT AND TRADEMARK OFFICE
CERTIFICATE OF CORRECTION

Page 1 of 1

PATENT NO. : 8,445,458 B2
APPLICATION NO. : 12/666617
DATED : May 21, 2013
INVENTOR(S) : Hageman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 504 days.

Signed and Sealed this
Sixteenth Day of December, 2014

Michelle K. Lee
*Deputy Director of the United States Patent and Trademark Office*

Adverse Decision in Interference

Patent No. 8,445,458, Robert Johan Joseph Hageman, Patrick Joseph Gerardus Hendrikus Kamphuis, and Ladislaus Maria Broersen, FOOD COMPOSITION FOR PRODROMAL DEMENTIA PATIENTS, Interference 106,096, final judgment adverse to patentees rendered, March 29, 2019, as to claims 1-10.

*(Official Gazette March 24, 2020)*